United States Patent [19]

Grove et al.

[11] Patent Number: 5,527,350

[45] Date of Patent: Jun. 18, 1996

[54] PULSED INFRARED LASER TREATMENT OF PSORIASIS

[75] Inventors: Robert E. Grove, Pleasanton; James Z. Holtz, Livermore, both of Calif.

[73] Assignee: Star Medical Technologies, Inc., Pleasanton, Calif.

[21] Appl. No.: 22,978

[22] Filed: Feb. 24, 1993

[51] Int. Cl.$^6$ ........................................................ A61N 5/06
[52] U.S. Cl. ............................... 607/89; 606/9; 606/3
[58] Field of Search ............................ 607/88–9; 606/3, 606/13, 9, 17

[56] References Cited

U.S. PATENT DOCUMENTS

| | | |
|---|---|---|
| 4,122,853 | 10/1978 | Smith . |
| 4,733,660 | 3/1988 | Itzkan ........................... 606/17 X |
| 4,829,262 | 5/1989 | Furumoto . |
| 4,874,361 | 10/1989 | Obagi ........................... 606/3 |
| 4,917,084 | 4/1990 | Sinofsky ........................ 607/89 X |
| 4,917,486 | 4/1990 | Raven et al. . |
| 4,930,504 | 6/1990 | Diamantopoulos ............. 607/88 |
| 4,996,046 | 2/1991 | Warshaw et al. .............. 424/78 |
| 5,108,388 | 4/1992 | Trokel ........................... 606/3 X |
| 5,217,455 | 6/1993 | Tan ............................... 606/3 X |

OTHER PUBLICATIONS

S. M. Hacker et al., "The Effect of Flash Lamp–Pulsed Dye Laser on Psoriasis", Archives of Dermatology, vol. 128, Jun. 1992, pp. 853–855.

J. E. Rasmussen, "Effect of Flash Lamp Pulsed Tunable Dye Laser on Psoriasis", Abstract presented at the One Hundred Twelfth Annual Meeting of the American Dermatological Association, Inc., Naples, Florida, 21–26 Feb. 1992.

J. Boulnois, "Photophysical Processes in Recent Medical Laser Developments: a Review", Lasers in Medical Science vol. 1 (1986) pp. 47–66.

E. K. Orenberg et al., "Comparison of heat delivery systems for hyperthermia treatment of psoriasis", Int. J. Hyperthermia, 1986 vol. 2, No. 3, pp. 231–241.

*Primary Examiner*—Angela D. Sykes
*Attorney, Agent, or Firm*—Wolf, Greenfield & Sacks

[57] ABSTRACT

A method for treating psoriasis with pulsed infrared laser illumination. A pulsed infrared diode laser having a wavelength of 800 nm and a pulse duration in the millisecond range selectively destroys abnormal blood vessels beneath psoriatic plaques at depths of up to one millimeter. Areas of approximately 0.5 cm$^2$ are sequentially treated. Uniform illumination intensity at a wide range of penetration depths allows selective destruction of the blood vessels without damage to the surrounding tissue, causing the psoriatic lesions to heal. The method may be applied more generally to the treatment of other dermal vascular malformations.

10 Claims, 3 Drawing Sheets

NORMAL SKIN

PSORLATIC SKIN

PULSED INFRARED LASER TREATMENT OF PSORIASIS

FIELD OF THE INVENTION

The invention relates generally to the treatment of psoriasis and more particularly to the use of a pulsed infrared laser source to treat psoriatic plaques.

BACKGROUND ART

Psoriasis is a chronic skin disease which afflicts about three percent of the U.S. population and has an incidence of one to three percent worldwide. It is characterized by dry, scaling plaques and often causes physical disfigurement and disability. There is no known cure for the disease and at present, no treatments which cause long-term remission. A variety of methods have been developed for reducing the severity of symptoms or inducing short-term remission. Several of these methods involve the use of light, at a variety of wavelengths, alone or in combination with topical or systemic pharmaceuticals.

The majority of sufferers generally report lessened symptoms during the summer months, presumably due to increased exposure to sunlight. Ultraviolet B light, one component of sunlight, has been used in conjunction with topical ointments such as extracts of coal tar as a treatment strategy. A more elaborate technique, referred to as PUVA, involves ultraviolet A light in conjunction with oral psoralen compounds. During PUVA treatment, patients are exposed to ultraviolet A light in a box similar to a tanning booth after ingesting the psoralen drug. Relief is temporary and treatment must be repeated after several months. This treatment has recently been associated with significantly higher rates of skin cancer.

Localized hyperthermia has also produced temporary clearing of psoriatic plaques. Several heat delivery systems have been investigated including infrared radiation from a sunlamp, ultrasound generation and hot water contact. Ultrasound hyperthermia provides the most uniform depthwise distribution of tissue heating.

Lasers have been employed in a variety of fundamentally different treatment approaches. These approaches include Ultraviolet delivery, photodynamic therapy and surgical excision.

Nitrogen lasers or excimer lasers have been used to replace the UV lamp in conventional light treatment approaches. This modification has not led to any reported benefits.

A tunable dye laser is used in photodynamic therapy to activate a photosensitive drug. Once activated the drug causes rapid cell death. The drug is administered systemically and serious side effects have been associated with its use.

Lasers have also been used as surgical tools in the treatment of psoriasis. A $CO_2$ or argon laser is used to burn away the psoriatic plaque. Surgical techniques involve considerable expense and require protracted healing time. There is also a substantial risk of scarring or postsurgical infection.

Laser photocoagulation and selective photothermolysis are well known. In photocoagulation, individual vessels are visually targeted. U.S. Pat. No. 4,917,486, Raven et al., describes a photocoagulation apparatus for ophthalmological use. Infrared light, which can be effectively filtered without affecting the operator's view, is used for safety reasons. U.S. Pat. No. 4,829,262, Furumoto, describes a tunable dye laser particularly suited to selective photothermolysis. The output wavelength is tunable to match some spectral property of the target tissue and the laser pulse duration is tailored to the size of the target. Efforts to perform selective photothermolysis of blood vessels are typically carried out in the visible region of the spectrum (typically around 577 nm) because hemoglobin absorbs very well in that range. Pulsed lasers (typically flashlamp-pumped dye lasers) have been successfully employed to close down unwanted vessels under the skin surface in the treatment of portwine stain birthmarks. The poor transmission of visible light through skin tissue makes it difficult to close deep vessels using a pulsed dye laser and repeated treatments are required.

Psoriatic skin tissue is created by the body at ten times the rate of normal healthy skin. This results in an epidermis which may become much thicker than normal, e.g. 0.5–0.7 mm. The underlying dermal papillae become elongated and capillaries proliferate. Although there is no general agreement among physicians as to the importance of microvessels in the development, persistence or recurrence of psoriasis, it has been suggested that eliminating these excess microvessels may provide long-term skin clearing. The elongated dermal papillae which contain the capillaries may extend as much as one millimeter below the skin surface. Conventional pulsed dye lasers operating in the visible range do not have adequate tissue penetration to reach these deep microvessels.

Attempts to clear psoriatic plaques using pulsed dye lasers have met with limited success. The laser fluence required is at or above the level normally considered to cause scarring in healthy skin. In one recent study, *Archives of Dermatology* 128:853–855 (1992), some improvement was obtained in slightly more than half the treated patients.

It is therefore an object of the present invention to provide an improved method for treating psoriatic plaques using selective photothermolysis to destroy underlying blood vessels at depths of up to one millimeter without causing thermal damage to surrounding tissue. Summary of the Invention The above object has been achieved in a method which selectively destroys subsurface microvessels with a pulsed infrared laser beam. A pulsed infrared laser light source, with an output wavelength in the range of 700 nm to 1100 nm is placed above a portion of the lesion and a laser pulse is triggered. The pulse duration is in the range of 200 microseconds to 20 milliseconds, with longer pulse durations targeting larger vessels. The laser pulse delivers a treatment fluence of 5 0to 50 joules per square centimeter at the skin surface. Skin transmission is high at these wavelengths, as is the relative absorption of blood in comparison with surrounding tissue. While the absolute absorption of blood is very low at these wavelengths, it still absorbs much more strongly than the surrounding tissue. Blood is therefore selectively heated causing damage to the endothelial cells lining the vessel wall. The target vessels cease to carry blood after illumination and are gradually removed in the same way a bruise is cleared. One or more laser pulses may be used to treat a specific portion of the plaque. The laser source is then repositioned over an untreated area and the process repeated until the entire lesion has been treated.

In the preferred embodiments, a semiconductor diode laser or semiconductor diode laser array with an output wavelength of approximately 800 nm is used. A pulse duration in the millisecond range is used to target vessels with diameters of 10 to 300 microns. Each laser pulse illuminates an area of approximately one-half square centimeter. No post-treatment dressing is required.

An advantage of the method of the present invention is that it selectively destroys blood vessels underlying psoriatic lesions at depths of up to one millimeter without excessive heating of the surrounding tissue.

DETAILED DESCRIPTION OF THE INVENTION

Figure 1A:
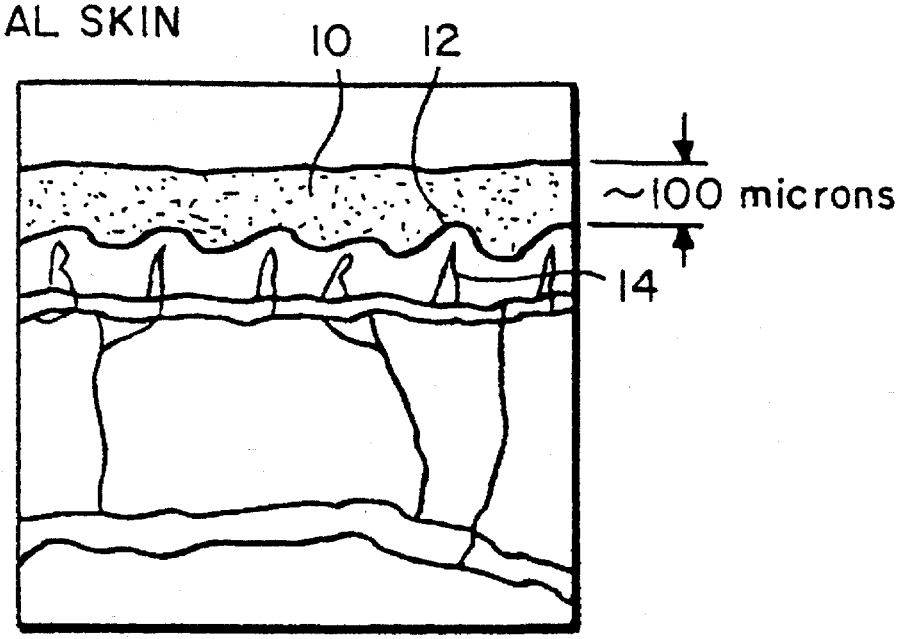
FIGS. 1a and 1b illustrate the structural difference between normal and psoriatic skin.
Figure 1B:
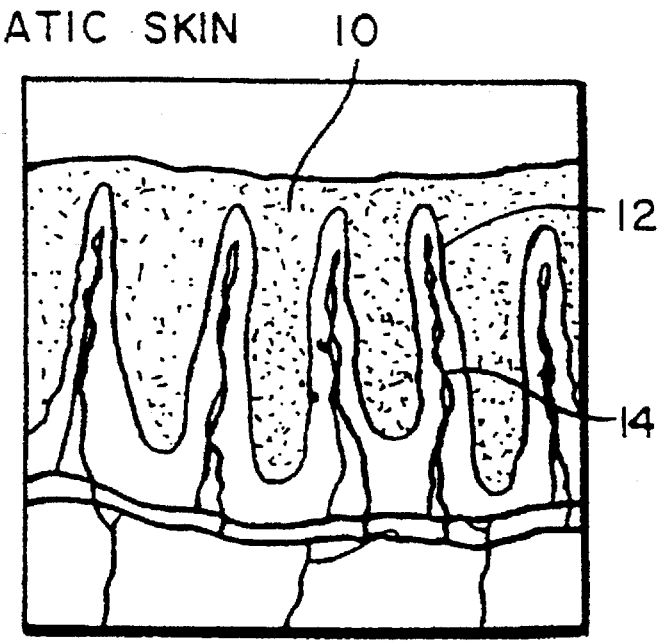

With reference to FIG. 1, the structural differences between normal and psoriatic skin are illustrated. Psoriasis is a chronic skin disorder of unknown origin. Psoriatic lesions, or plaques, are characterized by accelerated growth and loss of the normal maturation pattern of the epidermal keratinocytes. The epidermis 10 becomes thicker and the underlying dermal papillae 12 elongate. Capillary microvessels 14 dilate and proliferate. Dermal papillae 12 and associated microvessels 14 may extend to depths of up to one millimeter.

There is no general agreement among physicians as to the importance of these microvessels in the development, persistence or recurrence of psoriasis. Several articles suggest that the excessive vasculature is merely a side effect of an underlying, and as yet unknown, cause of the disease. Nonetheless, the present invention functions on the principle that selective destruction of the blood vessels underlying psoriatic plaques results in clearing of these lesions.

Figure 2:
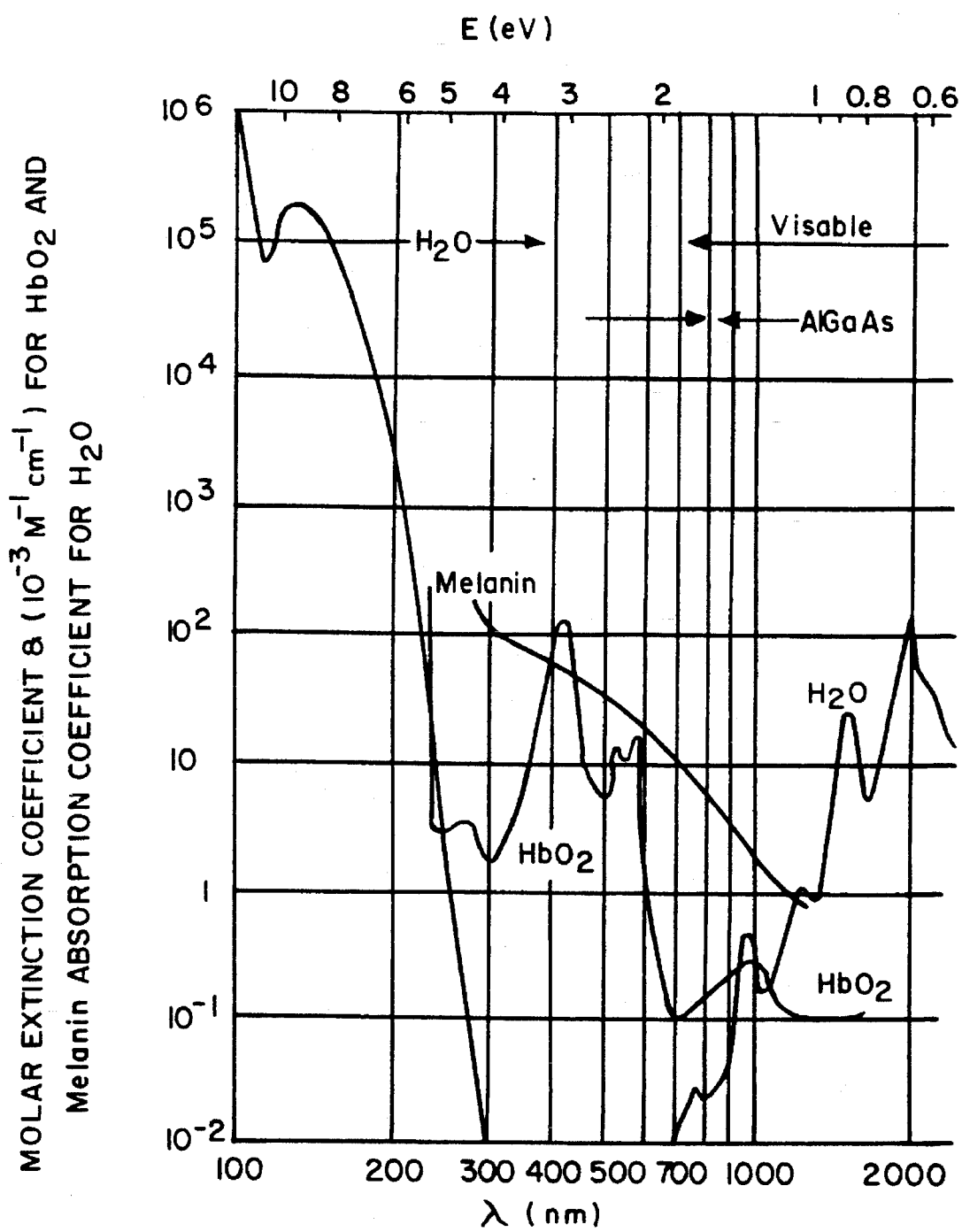
FIG. 2 is a plot indicating the absorption versus wavelength for skin tissue components.

To treat psoriasis by removing the excessive vasculature without collateral damage to surrounding tissue, deep tissue penetration and selective thermolysis of the blood vessels are required. Transmission of light through human skin is largely determined by scattering and by the absorption of various components within the tissue (e.g. hemoglobin, melanin and water). FIG. 2 is a plot indicating the absorption versus wavelength of skin tissue components, *Lasers in Medical Science*. Vol 1, (1986), pp. 47–66. Absorption varies over eight orders of magnitude for wavelengths ranging from 100 nm to 2000 nm. Because water is by far the largest single component of human tissue, the requirement for deep penetration through tissue (to depths of 1 mm) suggests wavelengths in the 300 nm to 1000 nm range, where water absorption is very low.

At wavelengths shorter than about 700 nm however, the absorption of light by melanin and by hemoglobin causes much of the incident light to be absorbed within a few hundred microns of the skin surface. The effort to get sufficient energy to deep vessels at wavelengths shorter than about 700 nm can easily cause explosion of surface vessels (for pulsed light) or burning of the skin (with continuous energy sources). Wavelengths in the 700 nm to 1100 nm range are preferred because skin tissue transmission at these wavelengths is high.

The achievement of selective photothermolysis of blood at wavelengths longer than 700 nm has been thought to be unachievable because of the very low absorption coefficient of blood in this wavelength band. At 800 nm, blood absorption is ~100 times less than at 577 nm, the typical wavelength used for selective photothermolysis on dermal tissue. Detailed analysis of remittance measurement on human skin, however, reveals that absorption in the 700–1100 nm wavelength range due to other components of dermal tissue is extremely low. Detailed analysis of light propagation and absorption reveals that energy can be deposited into the blood with remarkably high selectivity in the 700 to 1100 nm wavelength region, despite the fact that hemoglobin absorption is at its minimum in this wavelength band.

In the preferred embodiment, a commercially available AlGaAs semiconductor diode laser array (Spire Corp., Bedford, Mass.), is used. The output wavelength is ~800 nm. When a semiconductor diode array is used, a hollow tapered rectangular light guide directs the array output onto the treatment area. The preferred treatment area is ~0.5 cm$^2$ although any other convenient illumination area may be employed.

To achieve selective thermolysis, the target chromophore must be preferentially heated without excessive heating of the surrounding tissue. It is therefore necessary to illuminate the target for a time duration comparable to its thermal relaxation time. Long pulses can cause excessive heat to be conducted to tissues surrounding the target, causing bulk nonspecific thermal damage. In the preferred embodiment, the duration of the infrared laser pulse is in the millisecond range, corresponding to a target vessel size of 10 to 300 microns.

Figure 3A:
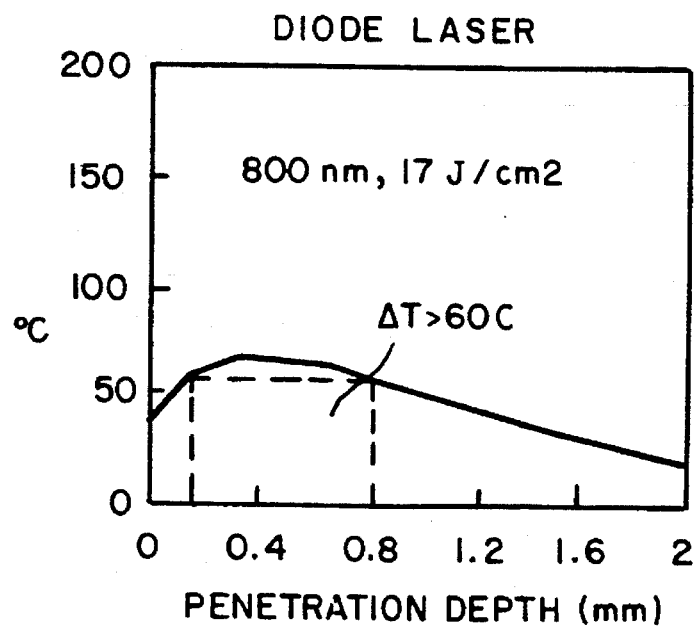
FIG. 3a is a plot of blood vessel temperature rise as a function of vessel depth for a diode laser.
Figure 3B:
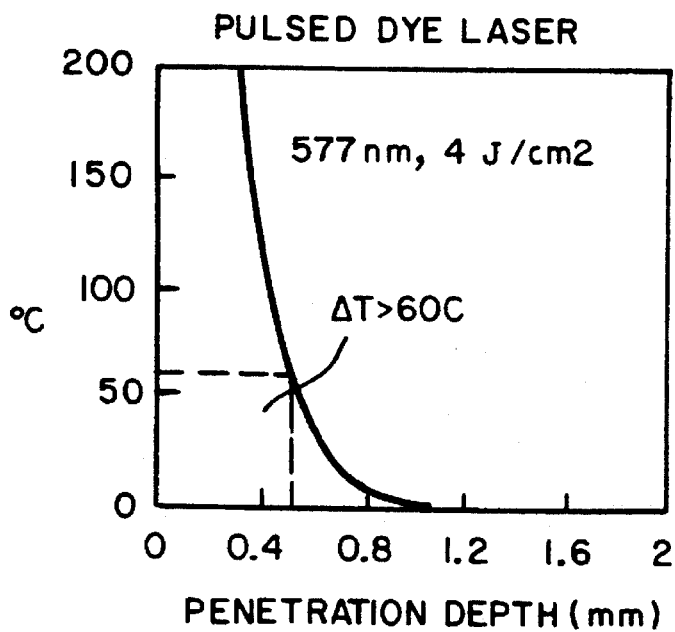
FIG. 3b is a plot of blood vessel temperature rise as a function of vessel depth for a pulsed dye laser.

Referring now to FIGS. 3a and 3b, the diode laser is preferred because it provides more uniform illumination and deeper penetration. The performance of each laser system was calculated for typical illumination conditions. The diode-array laser in FIG. 3a is operated with an illumination intensity of 17 J/cm$^2$ and a pulse duration of 5 milliseconds. The dye laser of FIG. 3b is operated with an illumination intensity of 4 J/cm$^2$ and a pulse duration of 360 microseconds. The temperatures that are shown reflect the peak vessel temperature that is reached at the end of the laser illumination. The dye laser has an output wavelength of 577 nm and the diodearray laser has an output wavelength of 800 nm. Because melanin absorption is much lower at 800 nm, much higher laser powers can be used without causing damage to the epidermis.

At 577 nm the illumination intensity is characteristic of exponential absorption. At 800 nm however, light scattering is much stronger than absorption (>100×) and the illumination intensity is more characteristic of diffusion. The more uniform and deeper penetration at 800 nm is expected to yield superior treatment performance for psoriasis or other vascular malformations.

One advantage of the present invention is that blood vessels at depths of up to one millimeter can be selectively destroyed without damage to the surrounding tissue.

Another advantage is that uniform illumination intensity is delivered over a wider range of penetration depths. Thus vessels may be treated to a greater depth in a single treatment, thereby reducing the number of treatments needed.

We claim:

1. A method for the treatment of psoriasis in human beings comprising the steps of:

aiming a laser so that the output of said laser impinges upon a psoriatic plaque, said output having a wavelength of between 700 nm and 1100 nm; and delivering one or more laser pulses having a fluence per pulse at the skin surface of between 5 joules per square centimeter and 50 joules per square centimeter, each of said pulses further having a pulse duration of between 0.2 millisecond and 20 milliseconds, whereby the blood vessels underlying said psoriatic plaque are selectively destroyed.

2. The method of claim 1 wherein aiming the laser includes a step of selecting the laser such that the laser emits light having the characteristics of an aluminum gallium arsenide semiconductor diode laser.

3. The method of claim 1 wherein said laser pulses impinge upon an area of between 0.1 square centimeter and 10 square centimeters.

4. The method of claim 1 further defined by said laser delivering one pulse.

5. The method of claim 1 further defined by repositioning said laser such that said output impinges upon untreated areas of said plaque until the entire area of said plaque has been treated.

6. A method for selectively destroying blood vessels contained in the dermis at depths of up to one millimeter comprising:

aiming a laser so that light from said laser impinges upon the dermis, said light having a wavelength between 700 nm and 1100 nm; and pulsing said laser so that each pulse delivers a fluence at the skin surface of between 5 joules per square centimeter and 50 joules per square centimeter, each of said pulses further having a pulse duration of between 0.2 millisecond and 20 milliseconds.

7. The method of claim 6 wherein aiming the laser includes a step of selecting the laser such that the laser emits light having the characteristics of an aluminum gallium arsenide semiconductor diode laser.

8. The method of claim 6 wherein said light impinges upon an area of between 0.1 square centimeter and 10 square centimeters.

9. The method of claim 8 further defined by repositioning said laser such that said light impinges upon untreated areas.

10. The method of claim 6 further defined by said laser delivering one pulse.

* * * * *